(12) United States Patent
Müllner et al.

(10) Patent No.: US 6,589,785 B1
(45) Date of Patent: Jul. 8, 2003

(54) DISRUPTING CELLS AND/OR TISSUE IN SOLID STATE IN PRESENCE OF SOLID DENATURING SUBSTANCE

(75) Inventors: Stefan Müllner, Langenfeld (DE); Thomas Neumann, Frankfurt (DE)

(73) Assignee: Aventis Research & Technologies GmbH & Co KG (DE)

( * ) Notice: Subject to any disclaimer, the term of this patent is extended or adjusted under 35 U.S.C. 154(b) by 0 days.

(21) Appl. No.: 09/581,563

(22) PCT Filed: Dec. 3, 1998

(86) PCT No.: PCT/EP98/07861
§ 371 (c)(1),
(2), (4) Date: Jul. 31, 2000

(87) PCT Pub. No.: WO99/31219
PCT Pub. Date: Jun. 24, 1999

(30) Foreign Application Priority Data

Dec. 16, 1997 (DE) .......................... 197 55 960

(51) Int. Cl.$^7$ .................. C12N 1/06; C12N 5/00; C12N 5/02
(52) U.S. Cl. ............... 435/325; 435/259; 435/410
(58) Field of Search ............ 435/262.5, 243, 435/1.3, 325, 410, 267, 259; 424/177.1, 400, 406

(56) References Cited

U.S. PATENT DOCUMENTS

| | | | |
|---|---|---|---|
| 4,476,049 A | 10/1984 | Kung | 260/112 R |
| 5,128,247 A | 7/1992 | Koller | 435/91 |
| 2002/0052026 A1 * | 5/2002 | Vicik | 435/69.5 |

FOREIGN PATENT DOCUMENTS

| | | |
|---|---|---|
| DE | 3731129 | 3/1988 |
| EP | 0138087 | 4/1985 |
| EP | 0291294 | 11/1988 |
| EP | 0387545 | 9/1990 |
| GB | 0648071 | 12/1950 |
| WO | 95/28409 | 10/1995 |

OTHER PUBLICATIONS

Morinaga Milk Inc. Co., Ltd., *Patent Abstract of Japan 6:* (122) : 57–050,884 Mar. 25, 1982.

* cited by examiner

*Primary Examiner*—David M. Naff
*Assistant Examiner*—Deborah K. Ware
(74) *Attorney, Agent, or Firm*—Connolly Bove Lodge & Hutz LLP

(57) ABSTRACT

A method for disrupting frozen cells and/or tissue in a solid, frozen state in the presence of a solid denaturing substance is provided. The method comprises providing frozen cells and/or tissue in frozen solid form, adding thereto the solid denaturing substance in sold form, and applying mechanical force thereto for disruption of the frozen cells and/or tissue. The frozen cells and/or tissue include muscle cells and/or muscle tissue, wheat cells and/or wheat tissue, and maize cells and/or maize tissue. Further, the solid, denaturing substance in solid form is a crystalline substance and can be selected from urea, thiourea, guanidium chloride, guanidium thiocyanate and ammonium sulfate. Also the solid, denaturing substance in solid form is added to the frozen cells and/or tissue in frozen form in an approximately 1 to 20 fold (w/w) excess.

16 Claims, No Drawings

DISRUPTING CELLS AND/OR TISSUE IN SOLID STATE IN PRESENCE OF SOLID DENATURING SUBSTANCE

BACKGROUND OF THE INVENTION

The invention relates to a method for disrupting biological material, in which the biological material is disrupted in the solid state and in the presence of a solid, denaturing substance.

When proteins, nucleic acids, fatty acids or other cell constituents are to be recovered, the cells have to be disrupted. A variety of methods and apparatus for disrupting cells have been developed, since the cells of various organisms differ in their behavior and, in some cases, can only be disrupted with difficulty. Also, the individual organisms or cells differ greatly with regard to the quality of the disruption. A particular problem when disrupting cells is the simultaneous liberation of degrading enzymes such as nucleases, proteases, lipases or glucosidases. In general, specific inhibitors are added to the batch to suppress such activities.

Usually, the cells are disrupted by means of ultrasound, French-press, high-pressure homogenizer or X-press while being suspended. To recover proteins, protease inhibitors such as, for example, PMSF, EDTA or leupeptin are generally added. However, the fact that the protease activity cannot always be suppressed sufficiently constitutes a disadvantage of these methods.

Solid cell material may also be comminuted in a mortar while cooling with liquid nitrogen, or in a vibration grinding mill (see, for example, Hess B. & Brand, K. (1983) Cell and Tissue Disintegration. General Aspects. In Methods Enzym. Anal., Third Ed., Eds. Bermeyer, H. U. VCI, Weinheim, FRG, Vol. 2, 26–30). However, the fact that the protein yields is relatively low compared with the other methods constitutes a disadvantage of this method.

To recover nucleic acids, the cells are generally disrupted by hydrolyzing the cell wall by means of lysozyme in the presence of SDS. The proteins are generally hydrolyzed by proteinase K. However, the fact that nucleic acids can only be recovered with difficulty from lysozyme-resistant cells constitutes a disadvantage of this method.

SUMMARY OF THE INVENTION

Object of the present invention was therefore to find a method which is widely applicable and allows cell constituents to be recovered in high yields.

Surprisingly, it has now been found that biological material can be disrupted readily in the solid state and in the presence of a solid, denaturing substance without degrading enzymes being activated.

Subject-matter of the present invention is therefore a method for disrupting biological material, in which the biological material is disrupted in the solid state and in the presence of solid, denaturing substance.

In a preferred embodiment, the solid, denaturing substance is a crystalline, preferably a crystalline organic, substance. Examples of especially preferred substances are urea, thiourea, guanidinium hydrochloride, guanidinium thiocyanate or ammonium sulfate. The disruption may also be carried out in the presence of various denaturing substances.

In general, the denaturing substance is employed in an approx. 1- to approx. 20-fold (w/w) excess, preferably in an approx. 1- to approx. 10-fold (w/w) excess and in particular in an approx. 1-fold (w/w) excess. It is furthermore advantageous for the biological material to be deep-frozen and preferably to remain deep-frozen during the disruption method according to the invention. Suitable for this purpose in an advantageous manner is, for example, liquid nitrogen.

In general, the biological material is disrupted by grinding, preferably in the presence, of a grinding ball.

Suitable as biological material is any biological material such as, for example, animal, human or plant cells, cell aggregates, tissues or animal, human or plant material. Also suitable are microorganisms such as fungi, bacteria, yeasts, protozoa or algae. Further suitable examples are *E. coli*, streptomycetes, Acremonium, Tetrahymena, Euglena, maize, wheat, muscle tissue or Actinoplanes.

To subsequently isolate the cell constituents such as proteins, nucleic acids (DNA, RNA), fatty acids, carbohydrates or the like after the disruption, the disrupted biological material is dissolved in a suitable buffer. The buffers which are customary for the cell type in question may be used for this purpose. The final concentration of urea is generally approx. 1 to approx. 10 M, preferably approx. 1 to approx. 5 M and especially approx. 4 M. It is advantageous to remove the cell debris and other solid constituents, for example by centrifugation, before the desired cell constituents are isolated by the methods known to the skilled worker.

DETAILED DESCRIPTION OF THE INVENTION

The method according to the invention is described hereinbelow in general terms and with reference to examples:

Usually, the organism or microorganism in question is grown in standard media known to the skilled worker. Thereafter, the cells can be harvested, for example by means of centrifugation. Then, they are usually washed and can be frozen for storage purposes. Plants can be grown on standard soils in the light or in the dark. Plant material is obtained, for example, by cutting of leaves, stalks or roots, which are usually immediately shock-frozen, for example in liquid nitrogen. Finally, the material can be comminuted mechanically by grinding in a nitrogen-cooled mortar.

The deep-frozen cell pellet, or the comminuted material, is then introduced into a shaking container consisting of, for example, teflon and cooled, for example using liquid nitrogen. The pellet is treated with, for example, urea in the abovementioned ratio. Advantageously, a grinding ball is then added, and the batch is shaken, for example in a laboratory vibration grinding mill, for example Dismembrator U, Braun Melsungen, Melsungen, FRG. Usually, the pellet is ground slowly in the presence of the urea by grinding at, for example, 2600 rpm, to give a powder. Advantageously, the batch is cooled with liquid nitrogen, and the procedure is repeated until a fine powder is obtained. After the disruption, the powder obtained is dissolved in a suitable buffer to the abovementioned final concentration of urea in order to isolate the cell constituents. The cell debris and other solid components are advantageously removed by centrifugation. The supernatant contains the desired cell constituents.

And important advantage of the method according to the invention is that cell constituents such as, for example, proteins, but also seaweed oil, can be recovered in high yields and in a simple manner, in particular from cells which are difficult to disrupt. In particular, it was possible to recover high-molecular weight (>20 kb) DNA was recovered in an advantageous fashion, for example from Actinoplanes, which are normally difficult to disrupt when using, for example, lysozyme. The DNA recovered in accordance with the invention is therefore also particularly suitable for isolating large DNA fragments. Also, optimization of the growing conditions for the microorganisms is generally not necessary in the method according to the invention.

The examples which follow are intended to illustrate the invention in greater detail without limiting it thereto.

EXAMPLES

1. Disruption of *E. coli*

*E. coli* was grown at 37° C. in a shaking flask in 100 ml of LB medium (10 g/l Bacto tryptone, 5 g/l yeast extract (Difco, Detroid, Mich., USA) and 5 g/l NaCl) to an OD 600 nm of 15. The cells were harvested by centrifugation for 15 minutes at 4000 rpm at 4° C. The supernatant was discarded. The pellet was washed twice in 1 M KCl solution. Then, the pellet obtained was frozen in liquid nitrogen. 2 g of the frozen pellet together with 2 g of urea were then transferred into a cooled teflon vessel in which a tungsten grinding ball (diameter 0.5 cm) was located, and ground for 1 minute in a vibration grinding mill (Dismembrator U, Braun Melsungen, Melsungen, FRG) at 2600 rpm. The vessel was cooled with liquid nitrogen, and the procedure was repeated several time (approximately 10 times). The protein yield amounted to 4 mg/g powder (urea content in the powder: 50%).

To isolate the protein, 2 g of the powder were dissolved in 2 ml of 10 mM Tris/HCl, 5 mM EDTA, 10 mM MgCl$_2$, pH 7.5. Then, the DNA was digested for 30 to 60 minutes by adding 10 units of benzonase or 10 µl of DNase/RNase solution (10 mg/ml DNaseI, 4 mg/ml RNaseA in 10 mM Tris/HCl$_2$, pH 7.5) at room temperature. The batch was then centrifuged at 14,000 rpm. The proteins were located in the supernatant and could be used in further experiments.

2. Disruption of *Streptomyces griseus*

*Streptomyces griseus* was grown for 2 days at 29° C. and 240 rpm in 50 ml of TSB (30 g/l tryptic soy broth) in a 1—1 baffle flask (Schott, Regensburg, FRG). The mycelium was harvested by centrifugation for 15 minutes at 5000 rpm and 4° C. Then, the pellet was washed in 1 M KCl. 2 g of the pellet together with 2 g of urea were transferred into a cooled teflon vessel in which a tungsten grinding ball (diameter 0.5 cm) was located, and ground for 1 minute in a vibration grinding mill (Dismembrator U, Braun Melsungen, Melsungen, FRG) at 2600 rpm. The vessel was cooled with liquid nitrogen, and the procedure was repeated several times (approximately 10 times). The protein yield amounts to 5 mg/g powder (urea content in the powder: 50%).

3. Disruption of *Acremonium chrysogenum*

*Acremonium chrysogenum* was grown for 3 days in minimal medium (30 g/l glycose, 3 g/l NaNO$_3$, 1 g/l K$_2$HPO$_4$, 0.5 g/l MgSO$_4$, 0.5 g/l KCl, 0.01 g/l FeSO$_4$) at 25° C. and 220 rpm. The cells were harvested by centrifugation for 15 minutes at 5000 rpm and 4° C. Then, the pellet was washed in 1 M KCl. 2 g of the pellet together with 2 g of urea were transferred into a cooled Teflon vessel in which a tungsten grinding ball (diameter 0.5 cm) was located, and ground for 1 minute in a vibration grinding mill (Dismembrator U, Braun Melsungen, Melsungen, FRG) at 2600 rpm. The vessel was cooled with liquid nitrogen, and the procedure was repeated several times (approximately 10 times). The protein yield amounted to 4.5 mg/g powder (urea content in the powder: 50%).

4. Disruption of *Tetrahymena thermophiles*

*Tetrahymena thermophiles* was grown for 2 days in PPYS medium (10 g/l protease peptone No. 3, 1 g/l yeast extract (Difco, Detroid, Mich., USA) and 1 ml/l trace elements (10 g/l sodium citrate, 24.3 g/l iron chloride) at 25° C. and 80 rpm. The cells were harvested by centrifugation at 2000 rpm and 4° C. The pellet was subsequently deep-frozen in liquid nitrogen. 2 g of the pellet together with 2 g of urea were transferred into a cooled Teflon vessel in which a tungsten grinding ball (diameter 0.5 cm) was located, and ground for 1 minute in a vibration grinding mill (Dismembrator U, Braun Melsungen, Melsungen, FRG) at 2600 rpm. The vessel was cooled with liquid nitrogen, and the procedure was repeated several times (approximately 10 times).

5. Disruption of *Euglena gracilis, Tetraselmis specialis, T. Chui* and *T. coneolutae*

*Euglena gracilis* was grown in medium 9 (1 g/l sodium acetate, 1 g/l meat extract, 2 g/l bacto tryptone, 2 g/l yeast extract, 0.02 g/l potassium nitrate, 0.002 g/l ammonium phosphate, 0.001 g/l magnesium sulfate, 0.04 g/l calcium chloride) and 30 ml of soil extract (300 g/l garden soil which had been boiled for 10 minutes, allowed to settle, then filtered and brought to pH 7.5 using a 10% strength sodium carbonate solution).

*Tetraselmis specialis, T. chui* or *T. coneolutae* were grown for 7 days at 25° C. and 100 rpm in medium 460 with half the salt concentration (0.3 g/l glucose, 0.01 g/l yeast extract (Difco, Detroid, Mich., USA), 11.74 g/l sodium chloride, 5.315 g/l magnesium chloride, 1.96 g/l disodium sulfate, 0.555 g/l calcium chloride, 0.33 g/l potassium chloride, 0.095 g/l sodium hydrogen carbonate, 0.05 g/l potassium bromide, 0.015 g/l boric acid, 0.02 g/l SrCl$_2$, 0.005 g/l iron (III) chloride, 0.025 g/l ammonium sulfate, 0.005 g/l dipotassium phosphate, 0.15 sodium glycerol phosphate, 3 g/l Tris buffer, 1.5 g/l glutamic acid) and 3 ml of a metal solution (1 g EDTA, 0.05 g/l FeCl$_3$, 0.15 g/l MnCl$_2$, 0.01 g/l ZnCl$_2$, 0.005 CoCl$_2$, 1 g/l H$_3$BO$_3$, brought to pH 6.5 with NaOH) and 1 ml of vitamin solution (0.003 g/l biotin, 1 g/l thiamine) in 100 ml in a 500-ml flask. The cells were harvested by centrifugation for 30 minutes at 2000 rpm and 4° C. Then, 0.5 g of moist biomass was treated with 0.5 g of urea and the mixture was transferred into a cooled Teflon vessel in which a tungsten grinding ball (diameter 0.5 cm) was located, and ground for 1 minute in a vibration grinding mill (Dismembrator U, Braun Melsungen, Melsungen, FRG) at 2600 rpm. The vessel was cooled with liquid nitrogen, and the procedure was repeated several times (approx. 10 times).

To recover the oil, the powder was treated with 4 ml of LM mixture (toluene/ethanol 1:1) and the mixture was incubated for 90 minutes at 40° C. with stirring. Then, the mixture was centrifuged for 30 minutes at 5000 rpm, and the upper, organic phase was removed. Then, the residue was treated with another 4 ml of LM mixture, shaken and centrifuged for 30 minutes at 5000 rpm. Again, the upper phase was removed and combined with the first organic phase. Then, the collected organic phases were concentrated in a rotary evaporator. The flask now contained the pure seaweed oil.

6. Disruption of Maize

Maize seeds (*Zea mays* cv. Felix) were sown in moist vermiculite soil and grown for 6 days at 30° C. in the light or in the dark (etiolated). The soil was always kept moist. The aerial parts of the plants were snipped off using scissors and immediately cooled in liquid nitrogen. Then, the plant material was divided into smaller sections with the aid of a surgical blade or else ground in a nitrogen-cooled mortar. However, the plant material may also be employed uncomminuted. Then, 2 g of plant material were treated with 2 g of urea and transferred into a cooled Teflon vessel in which a tungsten grinding ball (diameter 0.5 cm) was located, and ground for 1 minute in a vibration grinding mill (Dismembrator U, Braun Melsungen, Melsungen, FRG) at 2600 rpm. The vessel was cooled with liquid nitrogen, and the procedure was repeated several times (approximately 10 times). The protein yield amounted to 7.5 mg/g powder (urea content in the powder: 50%).

7. Disruption of Wheat

Wheat (*Triticum aestivum* cv. Ralle) seeds were sown in moist vermiculite soil and grown for 6 days at 30° C. in the light or in the dark (etiolated). The soil was always kept moist. The aerial parts of the plants were snipped off using scissors and immediately cooled in liquid nitrogen. Then, the plant material was divided into smaller sections with the aid of a surgical blade or else ground in a nitrogen-cooled mortar. However, the plant material may also be employed uncomminuted. Then, 2 g of plant material were treated with 2 g of urea and transferred into a cooled Teflon vessel in which a tungsten grinding ball (diameter 0.5 cm) was located, and ground for 1 minute in a vibration grinding mill (Dismembrator U, Braun Melsungen, Melsungen, FRG) at 2600 rpm. The vessel was cooled with liquid nitrogen, and the procedure was repeated several times (approximately 10 times). The protein yield amounted to 7.5 mg/g powder (urea content in the powder: 50%).

8. Disruption of Muscle Tissue

Muscles from rats or mice were frozen in liquid nitrogen immediately after the animals had died. Then, 2 g of deep-frozen muscle were mixed with 18 g of urea and transferred into a cooled Teflon vessel (volume 20 ml) in which a tungsten grinding ball (diameter 1 cm) is located, and ground for 1 minute in a vibration grinding mill (Dismembrator U, Braun Melsungen, Melsungen, FRG) at 2600 rpm. The vessel was cooled with liquid nitrogen, and the procedure was repeated several times (approx. 10 times). After the disruption, the powder contained 10% protein.

9. Isolation of Chromosomal DNA From *Actinoplanes utahensis*

The cultures were grown in 300-ml Erlenmeyer flasks containing 50 ml of R2YE medium [(Hopwood, D. A. et al. (1985) Genetic manipulation of Streptomyces: a laboratory manual. John Innes Foundation, Norwich, UK] at 28° C. and 180 rpm (5 days). The cell pellet (2 g) was harvested by centrifugation at 4° C., placed into a 5-ml disruption vessel (teflon) together with a tungsten carbite ball (diameter 0.5 cm) and 2 g of urea and frozen in liquid nitrogen. Then, the cell pellet was homogenized for 1 minute in the Dismembrator mill at 2600 rpm. After each cycle, the disruption vessel was cooled in liquid $N_2$. The process was repeated three times. The cold homogenizate was then resuspended in 20 ml of TSE buffer (TSE: 25 mM Tris/HCl; 25 mM EDTA, 10.3% sucrose pH 8.0) together with 10 µg/ml RNAse. The solution was subsequently treated with 10 ml of 2% SDS. Then, 7 ml of neutral $CHCl_3$/phenol (1:1) were added and the sample was mixed. The two phases were separated by centrifugation (4000 rpm, 10 minutes), and approximately 15 ml of the aqueous upper phase were removed carefully using a pipette. This was placed into a fresh tube and extracted once by treating with 3 ml of $CHCl_3$. After recentrifugation (4000 rpm, 10 minutes) and phase separation, the upper phase was treated with 1/10 volume 3 M sodium acetate (pH 5.2) and 0.8 volume of isopropanol and the DNA was precipitated. The DNA was then harvested from this solution by centrifugation at 15,000 g (30 minutes) or by fishing with a glass rod. The DNA was washed with 70% ethanol, then dried and taken up in TE buffer.

We claim:

1. A method for disrupting frozen cells and/or tissue, comprising the steps of:
    (a) providing frozen cells and/or tissue in frozen solid form;
    (b) adding a solid denaturing substance in solid form to the frozen cells and/or tissue in frozen solid form; and
    (c) applying mechanical force to disrupt the frozen cells and/or tissue in frozen form in the presence of the solid denaturing substance to release cell constituents comprising protein, nucleic acids, fatty acids and/or carbohydrates from the frozen cells and/or tissue without activating degrading enzymes.

2. The method as claimed in claim 1, wherein the solid, denaturing substance in solid form is a crystalline substance.

3. The method as claimed in claim 2, wherein the crystalline substance is a crystalline organic substance.

4. The method as claimed in claim 1, wherein the solid, denaturing substance in solid form is selected from the group consisting of urea, thiourea, guanidium chloride, guanidium thiocyanate and ammonium sulfate.

5. The method as claimed in claim 1, wherein the solid denaturing substance in solid form is added to the frozen cells and/or tissue in frozen solid form in an approximately 1- to approximately 20-fold (w/w) excess.

6. The method as claimed in claim 1, wherein the frozen cells and/or tissue in frozen solid form are deep-frozen.

7. The method as claimed in claim 1, wherein the frozen cells and/or tissue in frozen solid form are disrupted at low temperature.

8. The method as claimed in claim 7, wherein the frozen cells and/or tissue in frozen solid form are disrupted while cooling with liquid nitrogen.

9. The method as claimed in claim 1, wherein the frozen cells and/or tissue in frozen solid form are disrupted by grinding.

10. The method as claimed in claim 9, wherein the grinding is carried out with a grinding ball.

11. The method as claimed in claim 1, wherein the frozen cells and/or tissue in frozen solid form are selected from the group consisting of muscle cells and/or muscle issue, wheat cells and/or wheat tissue, and maize cells and/or maize tissue.

12. The method as claimed in claim 1, wherein the frozen cells and/or tissue in frozen solid form are selected from among microorganisms.

13. The method as claimed in claim 2, wherein the microorganisms are selected from the group consisting of fungi, bacteria, yeasts, protozoa and algae.

14. The method as claimed in claim 1, wherein after the disruption of the frozen cells and/or tissue in frozen solid form disrupted cells and/or tissue are subsequently suspended in a buffer.

15. The method as claimed in claim 14, wherein the buffer is added in an amount to provide a final concentration of the denaturing substance in the buffer of approximately 1 to 10 M, 1 to 5 M or 4M.

16. The method as claimed in claim 14, wherein after suspension of the disrupted cells and/or tissue in a buffer, the disrupted cells and/or tissue are centrifuged.

* * * * *

UNITED STATES PATENT AND TRADEMARK OFFICE
CERTIFICATE OF CORRECTION

PATENT NO.     : 6,589,785 B1                                    Page 1 of 1
DATED          : July 8, 2003
INVENTOR(S)    : Stefan Mullner et al.

It is certified that error appears in the above-identified patent and that said Letters Patent is hereby corrected as shown below:

<u>Column 6,</u>
Line 11, "frozen form" should read -- frozen solid form --.
Line 42, "issue" should read -- tissue --.

Signed and Sealed this

Sixteenth Day of September, 2003

JAMES E. ROGAN
*Director of the United States Patent and Trademark Office*